US009591987B1

(12) United States Patent
Liedtke (10) Patent No.: US 9,591,987 B1
(45) Date of Patent: Mar. 14, 2017

(54) DETERMINING BODY COMPOSITION THROUGH SEGMENTAL BIOELECTRICAL IMPEDANCE ANALYSIS (BIA)

(71) Applicant: RJL Systems, Inc., Clinton Township, MI (US)

(72) Inventor: Rudolph J. Liedtke, Grosse Pointe Park, MI (US)

(73) Assignee: RJL SYSTEMS, INC., Clinton Township, MI (US)

( * ) Notice: Subject to any disclaimer, the term of this patent is extended or adjusted under 35 U.S.C. 154(b) by 190 days.

(21) Appl. No.: 14/181,003

(22) Filed: Feb. 14, 2014

Related U.S. Application Data (60) Provisional application No. 61/869,283, filed on Aug. 23, 2013.

(51) Int. Cl.
*A61B 5/053* (2006.01)
(52) U.S. Cl.
CPC .................. *A61B 5/0537* (2013.01)
(58) Field of Classification Search
CPC .............................. A61B 5/0537; A61B 5/053
See application file for complete search history.

(56) References Cited

U.S. PATENT DOCUMENTS

| 3,871,359 A | 3/1975 | Pacela | 600/547 |
| 4,911,175 A | 3/1990 | Shizgal | 128/734 |
| 4,947,862 A | 8/1990 | Kelly | 128/734 |

(Continued)

FOREIGN PATENT DOCUMENTS

| JP | 63-109841 | 5/1988 |
| JP | 4-96733 | 3/1992 |
| JP | 2000-245705 | 9/2000 |
| JP | 2000-271101 | 10/2000 |

OTHER PUBLICATIONS

Ling, Carolina Hy, et al. "Accuracy of direct segmental multi-frequency bioimpedance analysis in the assessment of total body and segmental body composition in middle-aged adult population." Clinical Nutrition 30.5 (2011): 610-615.*

(Continued)

*Primary Examiner* — Michael C Stout
*Assistant Examiner* — Nicholas E Kolderman
(74) *Attorney, Agent, or Firm* — Christopher P. Maiorana, PC (57) ABSTRACT

An apparatus includes an analysis circuit and a controller. The analysis circuit may be configured to automatically make a plurality of segmental bioelectrical resistance and reactance measurements using permutations of a plurality of electrodes selected four at a time. The plurality of electrodes are configured to be attached to predetermined locations on a body of a subject. The controller may be configured to (i) calculate a plurality of segmental body composition values using the plurality of segmental bioelectrical resistance and reactance measurements, a number of predetermined coefficients, and a number of predictive equations, and (ii) generate a report presenting the plurality of segmental body composition values and a total body composition value. The number of predetermined coefficients are stored in a lookup table. Each of the segmental body composition values when added sum to a value essentially equal to respective whole body composition values.

20 Claims, 8 Drawing Sheets

(56) References Cited

U.S. PATENT DOCUMENTS

| | | | | |
|---|---|---|---|---|
| 5,063,937 | A | 11/1991 | Ezenwa et al. | 128/723 |
| 5,086,781 | A | 2/1992 | Bookspan | 128/734 |
| 5,088,489 | A | 2/1992 | Lerman | 60/7 |
| 5,335,667 | A | 8/1994 | Cha et al. | 128/734 |
| 5,371,469 | A | 12/1994 | Anderson | 324/705 |
| 5,449,000 | A | 9/1995 | Libke et al. | 128/734 |
| 5,503,157 | A | 4/1996 | Sramek | 128/693 |
| 5,615,689 | A * | 4/1997 | Kotler | A61B 5/0535 600/547 |
| 5,720,296 | A | 2/1998 | Cha | 128/734 |
| 5,749,369 | A | 5/1998 | Rabinovich et al. | 128/734 |
| 5,865,763 | A | 2/1999 | Kotler et al. | 600/547 |
| 6,011,992 | A | 1/2000 | Hubbard et al. | 600/547 |
| 6,256,532 | B1 | 7/2001 | Cha | 600/547 |
| 6,292,690 | B1 | 9/2001 | Petrucelli et al. | 600/547 |
| 6,339,722 | B1 | 1/2002 | Heethaar et al. | 600/547 |
| 6,442,422 | B1 | 8/2002 | Duckert | 600/547 |
| 6,473,641 | B1 | 10/2002 | Kodama et al. | 600/547 |
| 6,631,292 | B1 * | 10/2003 | Liedtke | A61B 5/053 600/547 |
| 7,003,346 | B2 | 2/2006 | Singer | 600/547 |
| 8,271,079 | B2 | 9/2012 | Cha et al. | 600/547 |
| 8,332,026 | B2 | 12/2012 | Cha et al. | 600/547 |
| 2009/0043222 | A1 * | 2/2009 | Chetham | A61B 5/0537 600/547 |
| 2010/0249642 | A1 * | 9/2010 | Cha | A61B 5/0537 600/547 |
| 2012/0302841 | A1 | 11/2012 | Coressel et al. | 600/301 |

OTHER PUBLICATIONS

Tanita, Body Composition Analyzer BC-418MA Instruction Manual, Aug. 9, 2002.*

J.M.H. Risser, et al., "A Comparison of Fat-free Mass Estimates in Men Infected With the Human Immunodeficiency Virus", Journal of Parenteral and Enteral Nutrition, vol. 19, No. 1, 1995, pp. 28-32.

Michael Ott, et al., "Bioelectrical Impedance Analysis as a Predictor of Survival in Patients with Human Immunodeficiency Virus Infection", Journal of Acquired Immune Deficiency Syndromes and Human Retrovirology, vol. 9, No. 1, 1995, pp. 20-25.

T.E.M.S. Sluys, et al., "Body Composition in Patients With Acquired Immunodeficiency Syndrome: A Validation Study of Bioelectric Impedance Analysis", Journal of Parenteral and Enteral Nutrition, vol. 17, No. 5, 1993, pp. 404-406.

Kotler, Donald P., et al., Prediction of body cell mass, fat-free mass, and total body water with bioelectrical impedance analysis: effects of race, sex, and disease[1-3], 1996 American Society for Clinical Nutrition, pp. 489S-497S.

* cited by examiner

DETERMINING BODY COMPOSITION THROUGH SEGMENTAL BIOELECTRICAL IMPEDANCE ANALYSIS (BIA)

This application relates to U.S. Ser. No. 61/869,283, filed Aug. 23, 2013, which is incorporated by reference in its entirety.

FIELD OF THE INVENTION

The present invention relates to biometric data generally and, more particularly, to a method and/or architecture for determining body composition through segmental bioelectrical impedance analysis (BIA).

BACKGROUND OF THE INVENTION

A human body is composed of water, muscle, bone and fat, in addition to small amounts of special components. The total of these elements constitutes the body weight. Quantitatively measuring the respective elements is called body composition analysis. The proportion occupied by the components other than fat is called fat free mass. Comparison between fat free mass and fat mass is used in identifying various adult diseases. In medical terms, of the body composition, fat free mass (FFM) is the main component for supporting the human body.

Patients suffering from a gradual loss of skeletal muscle mass (sarcopenia) because of aging and/or disease can be quantitatively assessed and identified. Wasting diseases (cachexia) and many health related conditions also result in a decrease of FFM. Furthermore, based on body composition analysis, the growth of children and the nutritional status of the elderly can be quantified.

The various conventional methods for measuring the body composition include (i) using hydrodensitometry, (ii) measuring the thickness of the sub-cutaneous fat layer by using a caliper or near infrared light, (iii) taking photographic images using methods such as nuclear magnetic resonance (NMR) and dual energy X-ray absorptiometry (DEXA), and (iv) using dilution methods such as heavy water ($D_2 0$) and bromide solution. Hydrodensitometry is highly accurate, and, therefore, is used as a standard method. However, hydrodensitometry is a troublesome task to carry out, and thus cannot be applied to the elderly or to a patient. Measuring the thickness of the sub-cutaneous fat layer has the disadvantage that the accuracy and repeatability is low. Nuclear magnetic resonance (NMR), dual energy X-ray absorptiometry (DEXA), and the dilution methods are expensive to carry out, and, therefore, cannot be applied to general patients in an economical manner.

Another method for measuring the body composition is bioelectrical impedance analysis (BIA). BIA is safe compared with the other conventional methods, the measuring cost is very low, and the measuring can be done in a fast manner. However, measurements made using conventional BIA techniques do not provide the accuracy or repeatability obtained using, for example, nuclear magnetic resonance (NMR), dual energy X-ray absorptiometry (DEXA), and the dilution methods.

It would be desirable to implement a method and/or architecture for determining body composition through segmental bioelectrical impedance analysis (BIA) that could provide accuracy similar to nuclear magnetic resonance (NMR), dual energy X-ray absorptiometry (DEXA), and the dilution methods.

SUMMARY OF THE INVENTION

The present invention concerns an apparatus including an analysis circuit and a controller. The analysis circuit may be configured to automatically make a plurality of segmental bioelectrical resistance and reactance measurements using permutations of the plurality of electrodes selected four at a time. The plurality of electrodes are configured to be attached to predetermined locations on a body of a subject. The controller may be configured to (i) calculate a plurality of segmental body composition values using the plurality of segmental bioelectrical resistance and reactance measurements, a number of predetermined coefficients, and a number of predictive equations, and (ii) generate a report presenting the plurality of segmental body composition values and a total body composition value. The number of predetermined coefficients are stored in a lookup table. Each of the number of predictive equations expresses a correlation between a respective segmental body composition value and one or more of the plurality of segmental bioelectrical resistance and reactance measurements, such that segmental body composition values when added sum to a value essentially equal to respective whole body composition values.

The objects, features and advantages of the present invention include providing a method and/or architecture for determining body composition through segmental bioelectrical impedance analysis (BIA) that may (i) generate segmental (regional) body composition values using segmental bioelectric impedance values, (ii) provide regional values which when added sum to respective whole body values, (iii) use a multiplexed BIA device that allows multi-zone and segmental measurements to be made quickly and easily, (iv) automatically select leads and scan multiple zones, (v) use stick on electrodes, (vi) store resistance and reactance data for subsequent analysis, and/or (vi) provide PDF report output format.

BRIEF DESCRIPTION OF THE DRAWINGS

These and other objects, features and advantages of the present invention will be apparent from the following detailed description and the appended claims and drawings in which:

DETAILED DESCRIPTION OF THE PREFERRED EMBODIMENTS

Figure 1:
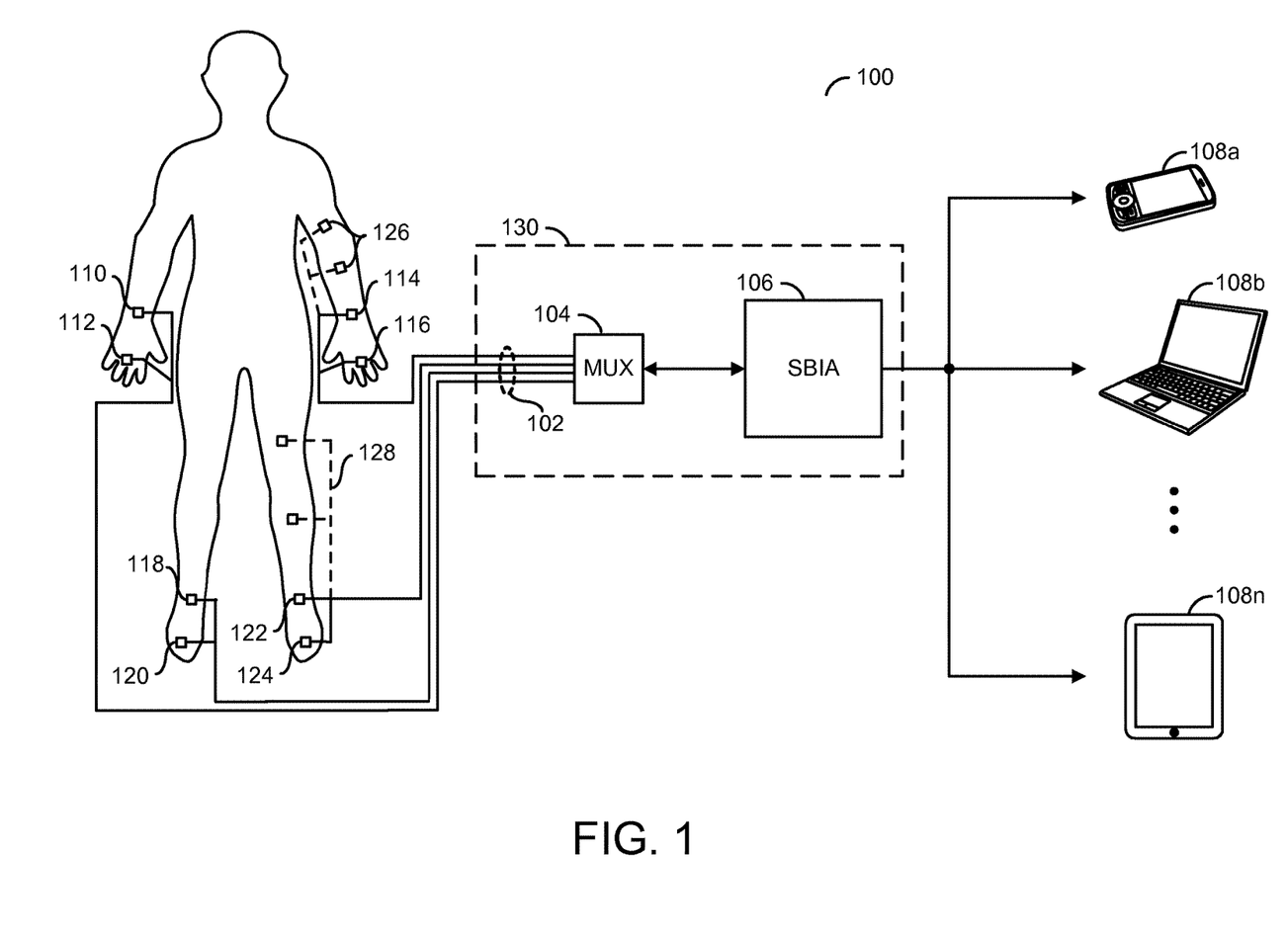
FIG. 1 is a diagram illustrating a system in accordance with an embodiment of the invention.

Referring to FIG. 1, a diagram of a system 100 is shown in accordance with a preferred embodiment of the present invention. In various embodiments, the system 100 may comprise a plurality of leads 102, a multiplexing circuit 104, an analysis circuit 106, and at least one of a number of electronic devices 108a-108n. The leads 102 are configured to connect the multiplex circuit 104 to a plurality of electrodes 110-124 attached to a subject. In various embodiments, each of the leads 102 clips to a respective one of the electrodes 110-124. In one example, the electrode 110-124 comprise stick on electrodes similar to electrodes used for taking electrocardiograms (EKGs). The stick on electrodes generally avoid high impedance bony structures on the wrist, the fingers of the hand, the ankle, and the bottoms of the feet of the subject, which improves measurement accuracy, repeatability, and segmental body composition results.

The electrodes 110, 114, 118, and 122 are configured as detecting electrodes and the electrodes 112, 116, 120, and 124 are configured as signal injection electrodes. The detecting electrode 110 is placed on an imaginary line bisecting the ulnar head (bone on the little finger side of the wrist) of the right arm of the subject. The detecting electrode 114 is placed on an imaginary line bisecting the ulnar head (bone on the little finger side of the wrist) of the left arm of the subject. The detecting electrode 118 is placed on an imaginary line bisecting the medial mallous (bone on the big toe side of the ankle) of the right leg of the subject. The detecting electrode 122 is placed on an imaginary line bisecting the medial mallous (bone on the big toe side of the ankle) of the left leg of the subject. The current source electrode 112 is placed at the base of the middle finger of the right hand. The current source electrode 116 is placed at the base of the middle finger of the left hand. The current source electrode 120 is placed at the base of the second toe of the right foot. The current source electrode 124 is placed at the base of the second toe of the left foot.

Depending upon the segments to be measured, the detecting electrodes may be placed in other locations on the subject. For example, the detecting electrodes 110 and 114 may be placed at other points (e.g., locations 126, etc.) on their respective arms and the detecting electrodes 118 and 122 may be placed at other points (e.g., locations 128, etc.) on their respective legs. In one example, a particular testing session may include taking a number of groups of measurements, where the detecting electrodes are placed in different positions before each group of measurements is taken.

The multiplexing circuit 104 is configured to isolate the subject from direct contact with any active circuits or ground paths that may cause stray undefined readings. In various embodiments, the multiplexer circuit 104 comprises a 2500 Volt isolated low capacitance eight lead 12 channel multiplexer. The multiplexer circuit 104 couples the signals carried by the leads 102 to the analysis circuit 106. The multiplexer circuit 104 is configured to allow the analysis circuit to select sets of the leads 102 to allow multi-zone and segmental measurements to be taken quickly and easily. In one example, the multiplexer circuit 104 and the analysis circuit 106 may be combined (integrated) into a single unit 130.

In various embodiments, the analysis circuit 106 comprises an analog portion (e.g., BIA circuitry) and a digital portion (e.g., hardware and/or software) configured to automatically handle selecting the leads, scanning multiple zones, and generating and storing resistance and reactance data. In various embodiments, the resistance and reactance data includes, but is not limited to right body resistance and reactance values, left body resistance and reactance values, lower body resistance and reactance values, upper body resistance and reactance values, right arm resistance and reactance values, left arm resistance and reactance values, right leg resistance and reactance values, left leg resistance and reactance values, right torso resistance and reactance values, left torso resistance and reactance values, transverse right arm to left leg resistance and reactance values, transverse left arm to right leg resistance and reactance values, and whole body resistance and reactance values.

The analysis circuit 106 is further configured to communicate the resistance and reactance data to one or more electronic devices 108a-108n. The resistance and reactance data may be communicated concurrently with the testing or downloaded at a later time. In addition to the BIA data, the analysis circuit 106 may be further configured to collect and store information (e.g., height, weight, age, gender, etc.) about the particular subject. In one example, the resistance and reactance values are communicated in a comma separated value (CSV) format. In some embodiments, the analysis circuit 106 may be connected to the electronic devices 108a-108n via a serial connection such as a universal serial bus (USB), IEEE 802.2 Ethernet, or other wired connection. In some embodiments, the analysis circuit 106 may be connected to the electronic devices 108a-108n via a wireless protocol (e.g., IEEE 802.11a/b/g/n, IEEE 802.15.4, ZIG-BEE, IEEE 802.15.1 BLUETOOTH, etc.). However, other communications protocols may be implemented accordingly to meet the design criteria of a particular implementation. In one example, the circuit 106 may be implemented using an analyzer as described in U.S. Pat. No. 6,631,292, which is incorporated by reference in its entirety.

The electronic devices 108a-108n may comprise one or more of a mobile computing device 108a, a laptop computer 108b, a desktop computer, a tablet computer 108n, etc. In various embodiments, the electronic devices 108a-108n are configured by application software to calculate a plurality of segmental body composition values using the information about the subject and the plurality of segmental bioelectrical resistance and reactance measurements received from the analysis circuit 106, a number of predetermined coefficients, and a number of predictive equations. The electronic devices 108a-108n are configured by the application software to generate a report presenting the plurality of segmental body composition values and a whole body composition value (e.g., on a display screen, as a PDF formatted report, as a printed report, etc.) in numerical and/or graphical form, and demonstrating that a sum of segmental body composition values is essentially equal to the respective whole body composition value.

In various embodiments, the predictive equations comprise sets of equations for determining body composition values corresponding to the whole body of the subject and each body segment of the subject. In various embodiments, the body composition values include values corresponding to lean mass, total mass, mass without bone (no bone mass), and fat mass for right and left arms, right and left legs, right and left sides, right and left torso segments, upper and lower body segments, and the whole body. The equation for determining a right arm lean mass (RALM) value is of the form RALM=AR1*exp(AR2*log(right arm resistance)+AR3*log(Height)−AR4)+AR5*Weight−AR6. The equation for determining a left arm lean mass (LALM) value is of the form LALM=AL1*exp(AL2*log(left arm resistance)+AL3*log(Height)−AL4)+AL5*Weight−AL6. The equation for determining a right arm mass (RAM) value is of the form RAM=exp(AR7*log(Weight)+AR8*log(RALM)−AR9). The equation for determining a left arm mass (LAM) value is of the form LAM=exp(AL7*log(Weight)+AL8*log (LALM)−AL9). The equation for determining a right arm no bone mass (RANBM) value is of the form RANBM=exp (AR10*log(Weight)+AR11*log(RALM)−AR12). The equation for determining a left arm no bone mass (LANBM) value is of the form LANBM=exp(AL10*log(Weight)+AL11*log(LALM)−AL12). The equation for determining a right arm fat mass (RAFM) value is of the form RAFM=RANBM−RALM. The equation for determining a left arm fat mass (LAFM) value is of the form LAFM=LANBM−LALM. The coefficients AR1, . . . , AR12, AL1, . . . , AL12 represent predetermined coefficients that may be read from a lookup table (LUT). In one example, the coefficients AR1, . . . , AR12, AL1, . . . , AL12 may have values of approximately 0.861, −1.208, 2.691, 5.959, 0.007, 0.137, 0.946, 0.195, 2.806, 0.991, 0.166, 3.016, 0.863, −1.259, 2.457, 4.483, 0.007, 0.126, 0.893, 0.254, 2.673, 0.928, 0.235, 2.846, respectively.

The equation for determining a right leg lean mass (RLLM) value is of the form RLLM=BR1*exp(BR2*log (right leg resistance)+BR3*log(Height)−BR4)+BR5*Weight−BR6. The equation for determining a left leg lean mass (LLLM) value is of the form LLLM=BL1*exp (BL2*log(left leg resistance)+BL3*log(Height)−BL4)+BL5*Weight−BL6. The equation for determining a right leg mass (RLM) value is of the form RLM=exp(BR7*log (Weight)+BR8*log(RLLM)−BR9). The equation for determining a left leg mass (LLM) value is of the form LLM=exp (BL7*log(Weight)+BL8*log(LLLM)−BL9). The equation for determining a right leg no bone mass (RLNBM) value is of the form RLNBM=BR10*(Weight)+BR11. The equation for determining a left leg no bone mass (LLNBM) value is of the form LLNBM=BL10*(Weight)+BL11. The equation for determining a right leg fat mass (RLFM) value is of the form RLFM=BR12*(RLNBM−RLLM)−BR13*(Gender)+BR14. The equation for determining a left leg fat mass (LLFM) value is of the form LLFM=BL12*(LLNBM−LLLM)−BL13*(Gender)+BL14. The coefficients BR1, . . . , BR14, BL1, . . . , BL14 represent predetermined coefficients that may be read from a lookup table (LUT). In one example, the coefficients BR1, . . . , BR14, BL1, . . . , BL14 may have values of approximately 0.657, −0.809, 3.065, 9.201, 0.044, 0.552, 0.868, 0.044, 1.343, 0.144, 0.779, 1.086, 0.720, 0.078, 0.613, −0.758, 3.207, 10.214, 0.050, 0.680, 0.833, 0.083, 1.273, 0.146, 0.689, 1.076, 0.748, 0.130, respectively.

The equation for determining a right side lean mass (RSLM) value is of the form RSLM=CR1*exp(CR2*log (right body resistance)+CR3*log(Height)−CR4)+CR5*Weight−CR6. The equation for determining a left side lean mass (LSLM) value is of the form LSLM=CL1*exp (CL2*log(left body resistance)+CL3*log(Height)−CL4)+CL5*Weight−CL6. The equation for determining a right side mass (RSM) value is of the form RSM=exp(CR7*log (Weight)+CR8*log(RSLM)−CR9). The equation for determining a left side mass (LSM) value is of the form LSM=exp(CL7*log(Weight)+CL8*log(LSLM)−CL9). The equation for determining a right side no bone mass (RSNBM) value is of the form RSNBM=CR10*(Weight)+CR11. The equation for determining a left side no bone mass (LSNBM) value is of the form LSNBM=CL10*(Weight)+CL11. The equation for determining a right side fat mass (RSFM) value is of the form RSFM=RSNBM−RSLM. The equation for determining a left side fat mass (LSFM) value is of the form LSFM=LSNBM−LSLM. The coefficients CR1, . . . , CR14, CL1, . . . , CL14 represent predetermined coefficients that may be read from a lookup table (LUT). In one example, the coefficients CR1, . . . , CR14, CL1, . . . , CL14 may have values of approximately 0.878, −0.832, 2.512, 4.465, 0.040, 0.063, 0.979, 0.029, 0.705, 0.481, 0.377, 0.836, −0.778, 2.454, 4.501, 0.053, 0.004, 0.979, 0.006, 0.595, 0.470, 0.417, respectively.

The equation for determining an upper body lean mass (UBLM) value is of the form UBLM=DU1*exp(DU2*log (upper body resistance)+DU3*log(Height)−DU4)+DU5*Weight−DU6. The equation for determining a lower body lean mass (LBLM) value is of the form LBLM=DL1*exp(DL2*log(lower body resistance)+DL3*log(Height)−DL4)+DL5*Weight−DL6. The equation for determining an upper body mass (UBM) value is of the form UBM=DU7*(Weight)−DU8*(Gender)+DU9. The equation for determining a lower body mass (LBM) value is of the form LBM=DL7*(Weight)−DL8*(Gender)+DL9. The equation for determining an upper body no bone mass (UBNBM) value is of the form UBNBM=DU10*(Weight)−DU11*(Gender)+DU12. The equation for determining a lower body no bone mass (LBNBM) value is of the form LBNBM=DL10*(Weight)−DL11*(Gender)+DL12. The equation for determining an upper body fat mass (UBFM) value is of the form UBFM=UBNBM−UBLM. The equation for determining a lower body fat mass (LBFM) value is of the form LBFM=LBNBM−LBLM. The coefficients DU1, . . . , DU12, DL1, . . . , DL12 represent predetermined coefficients that may be read from a lookup table (LUT). In one example, the coefficients DU1, . . . , DU12, DL1, . . . , DL12 may have values of approximately 0.861, −1.239, 2.553, 3.527, 0.014, 0.257, 0.132, 0.432, 1.371, 0.129, 0.352, 1.434, 0.632, −0.794, 3.124, 8.342, 0.094, 1.205, 0.310, 0.812, 1.412, 0.301, 0.980, 1.137, respectively.

The equation for determining a right torso lean mass (RTLM) value is of the form RTLM=RSLM−(RALM+RLLM). The equation for determining a left torso lean mass (LTLM) value is of the form LTLM=LSLM−(LALM+LLLM). The equation for determining a right torso mass (RTM) value is of the form RTM=RSM−(RAM+RLM). The equation for determining a left torso mass (RTM) value is of the form LTM=LSM−(LAM+LLM). The equation for determining a right torso no bone mass (RTNBM) value is of the form RTNBM=RSNBM−(RANBM+RLNBM). The equation for determining a left torso no bone mass (RTNBM) value is of the form LTNBM=LSNBM−(LTNBM+LTNBM). The equation for determining a right torso fat mass (RTFM) value is of the form RTFM=RTNBM−(RSLM−RALM−RLLM). The equation for determining a left torso fat mass (LTFM) value is of the form LTFM=LTNBM−(LSLM−LALM−LLLM).

The equation for determining a whole body lean mass (WBLM) value is of the form WBLM=E1*exp(E2*log(avg (right body resistance+left body resistance))+E3*log (Height)−E4)+E5*Weight−E6. The equation for determining a whole body mass (WBM) value is of the form WBM=E7*(Weight)−E8*(Gender)+E9. The equation for determining a whole body no bone mass (WBNBM) value is the form WBNBM=E10*(Weight)−E11*(Gender)+E12. The equation for determining a whole body fat mass (WBFM) value is of the form WBFM=WBNBM−WBLM. The coefficients E1, . . . , E12 represent predetermined coefficients that may be read from a lookup table (LUT). In one example, the coefficients E1, . . . , E12 may have values of approximately 0.862, −0.814, 2.465, 3.643, 0.089, 0.050, 0.978, 0.219, 0.805, 0.957, 0.617, 0.168, respectively.

Figure 2:
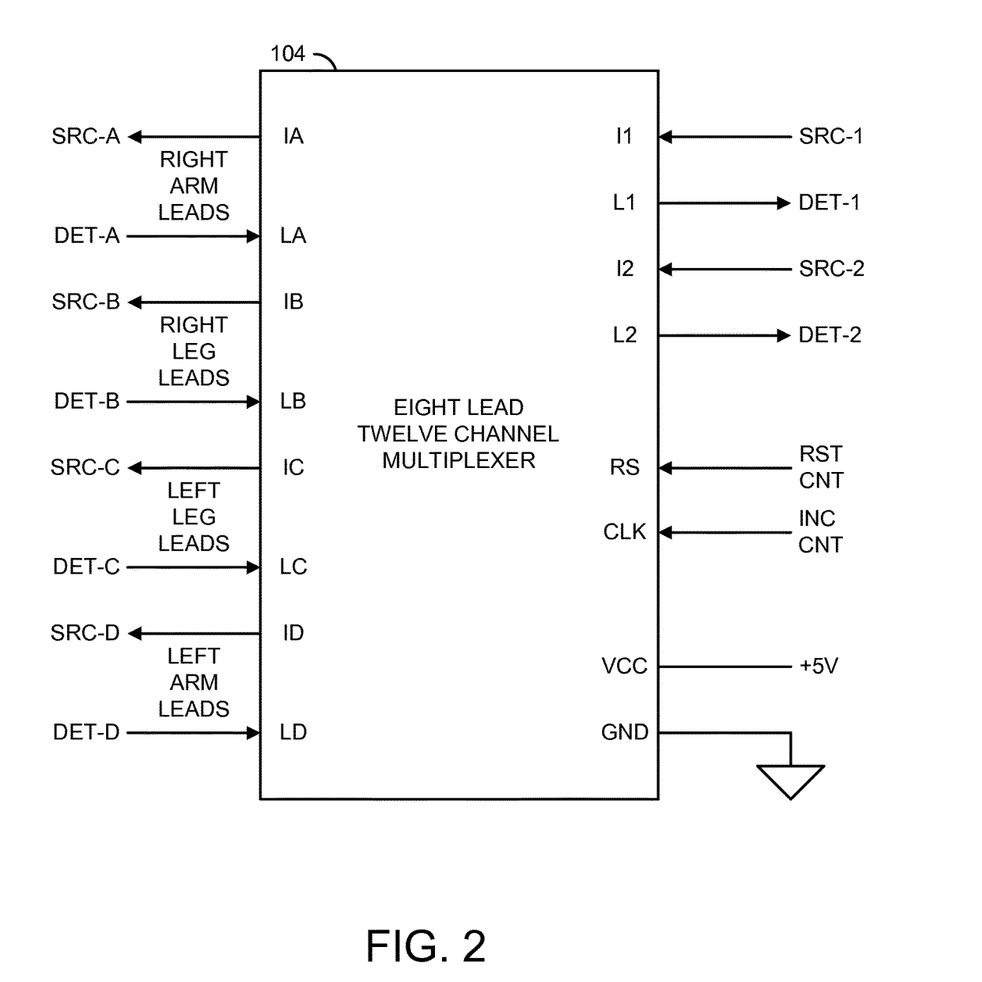
FIG. 2 is a diagram illustrating a multiplexer circuit of FIG. 1 in accordance with an embodiment of the invention.

Referring to FIG. 2, a diagram is shown illustrating inputs and outputs of an example implementation of the multiplexer circuit 104 of FIG. 1. In one example, the circuit 104 may be implemented as an eight-lead twelve-channel multiplexer configured to connect to eight subject leads (e.g., SRC-A, DET-A, SRC-B, DET-B, SRC-C, DET-C, and SRC-D, DET-D) to four analysis leads (e.g., SRC-1, DET-1, SRC-2, and DET-2). The circuit 104 may have an input RS that may receive a signal (e.g., RST CNT) and an input CLK that may receive a signal (e.g., INC CNT). The signals RST CNT and INC CNT may be used to control the connection of the subject leads to the analysis leads. In various embodiments, the signal INC CNT may be configured to increment or shift data of an internal counter, shift register, or decoder of the circuit 104 and the signal RST CNT may be configured to reset the stored value of the internal counter, shift register, or decoder. However, other methods of controlling the connection of the subject leads to the analysis leads may be implemented to meet the design criteria of a particular implementation.

Figure 3:
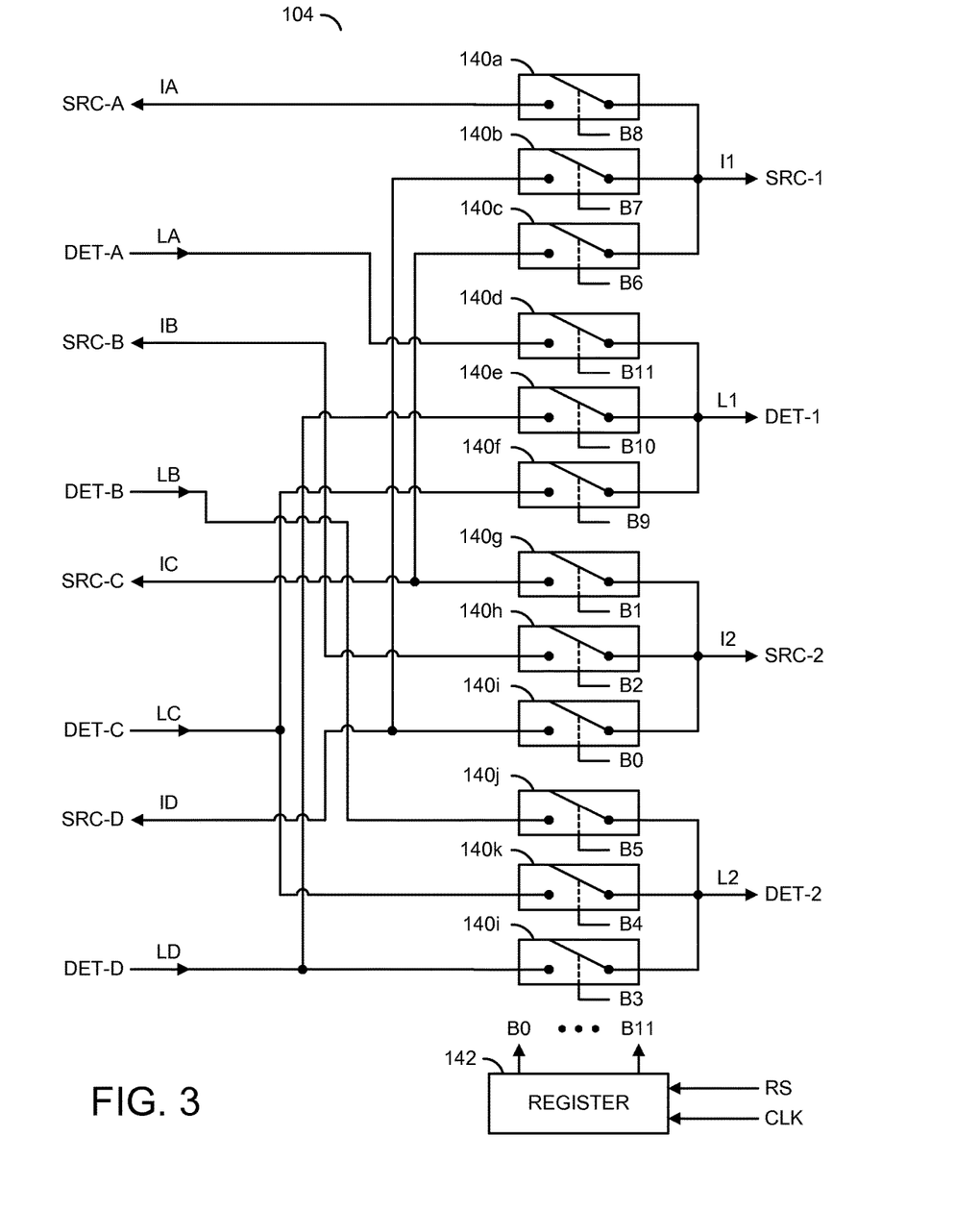
FIG. 3 is a diagram illustrating an example implementation of the multiplexer circuit of FIG. 2.

Referring to FIG. 3, a diagram is shown illustrating an example implementation of the multiplexer circuit 104 of FIG. 1. In one example, the circuit 104 may comprise a number of switches 140a-140i and a register 142. In some embodiments, the number of switches is twelve and the register 142 is implemented as part of a 12-bit binary counter or shift register. Output bits of the register 142 are used to control respective ones of the switches 140a-140i. In an embodiment implementing twelve switches, each analysis lead connects to a group of three switches and each subject lead connects to at least one of the switches.

Figure 4:
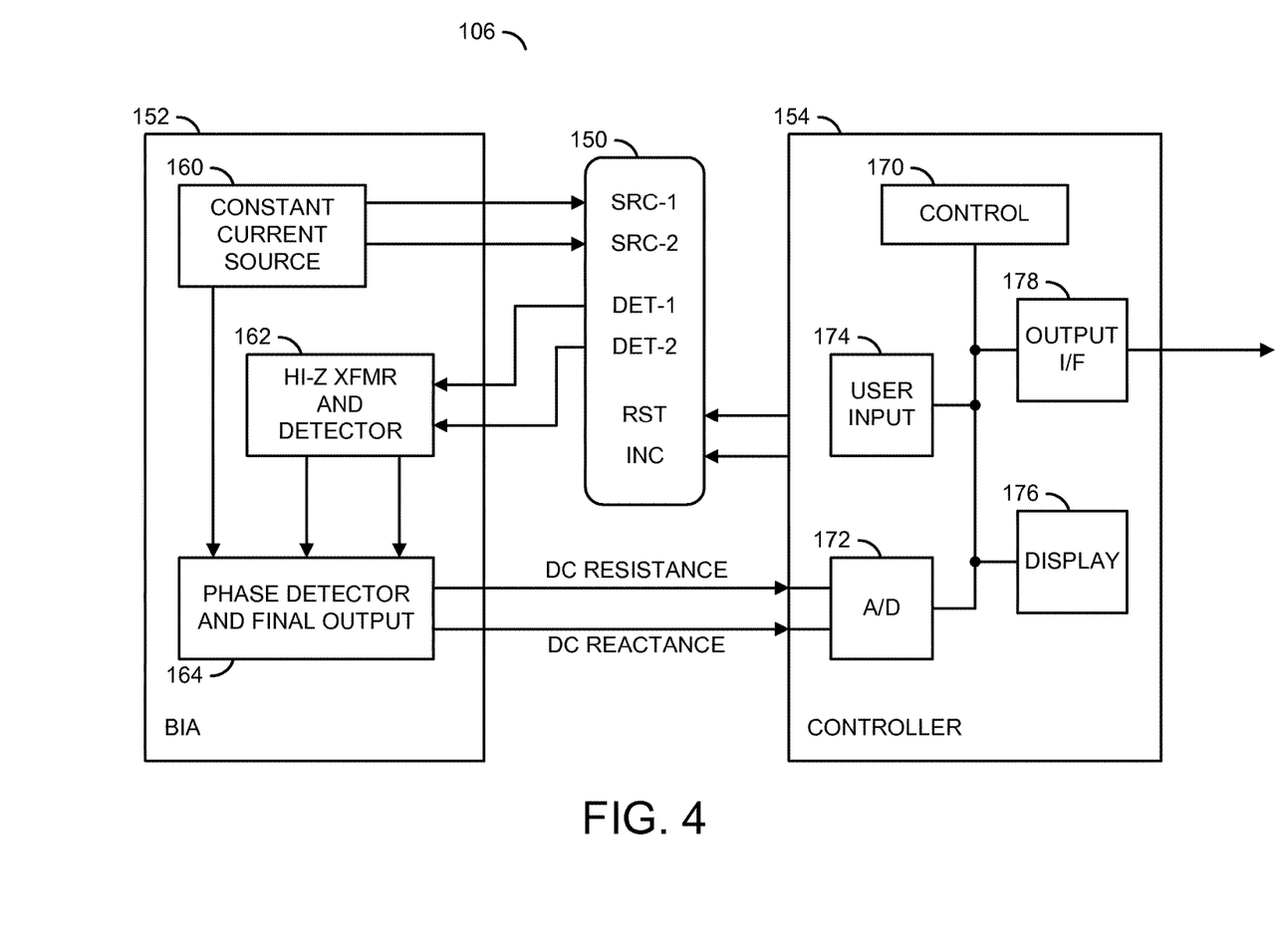
FIG. 4 is a diagram illustrating an analysis circuit of FIG. 1 in accordance with an embodiment of the invention.

Referring to FIG. 4, a diagram is shown illustrating an example implementation of the analysis circuit 106 of FIG. 1. The circuit 106 may be configured to connect to the circuit 104 using an interface 150. In one example, the circuit 106 may comprise a block (or circuit) 152 and a block (or circuit) 154. The block 152 may implement an analog portion of the circuit 106. The block 154 may implement a digital portion of the circuit 106. In one example, the circuit 152 implements circuitry for producing bioelectrical measurements comprising DC resistance and DC reactance values. In one example the circuit 154 implements an analog-to-digital (A/D) and controller portion of the circuit 106. The circuit 154 may be configured to convert analog resistance and reactance measurements made by the circuit 152 into digital resistance and reactance values that can be stored and/or communicated to the electronic devices 108a-108i.

In various embodiments, the circuit 152 comprises a block (or circuit) 160, a block (or circuit) 162, and a block (or circuit) 164. The block 160 may implement a constant current source and subject coupling transformer circuit. The block 162 may implement a high-impedance subject coupling transformer and detector circuit. The block 164 may implement a phase detector and final output circuit. The circuit 160 may provide the signals SRC-1 and SRC-2 to the interface 150. The circuit 162 may receive the signals DET-1 and DET-2 from the interface 150. The circuit 164 may be configured to generate analog resistance and reactance measurements in response to signals received from the circuits 160 and 162.

In various embodiments, the circuit 154 comprises a block (or circuit) 170, a block (or circuit) 172, a block (or circuit) 174, a block (or circuit) 176, and a block (or circuit) 178. The block 170 may implement a control circuit. The block 172 may implement an analog-to-digital (A/D) convertor circuit. The block 174 may implement a user input circuit. The block 176 may implement a display. The circuit 178 may implement an output interface (I/F). The control circuit 170 is generally configured to manage (i) operation of the multiplexer circuit 104 (e.g., via the signals RST CNT and INC CNT), (ii) operation of the analysis circuit 106, and (iii) communications with the user and the electronic devices 108a-108i. The circuit 172 may be configured to convert analog resistance and reactance measurements received from the circuit 152 to digital resistance and reactance values. The user input circuit 174 generally allows a user (technician) to enter information (e.g., age, height, weight, gender, etc.) about a subject and select menu items. For example, the user may select from menu items including, but not limited to, BIA Readings, Get BIA Zone Data, Display Zone Data, BIA Lead Change, Send Data to External Device, System Status, Options, etc. The display circuit 176 generally allows the user to interact with the analysis circuit 106 via menu screens and read the measured resistance and reactance values. For example, the user may start a scan to obtain segmental BIA values by selecting the Get BIA Zone Data menu. The output I/F circuit 178 generally allows the subject information and measured resistance and reactance values to be communicated to external devices (e.g., by selecting the Send Data to External Device menu).

Figure 5:
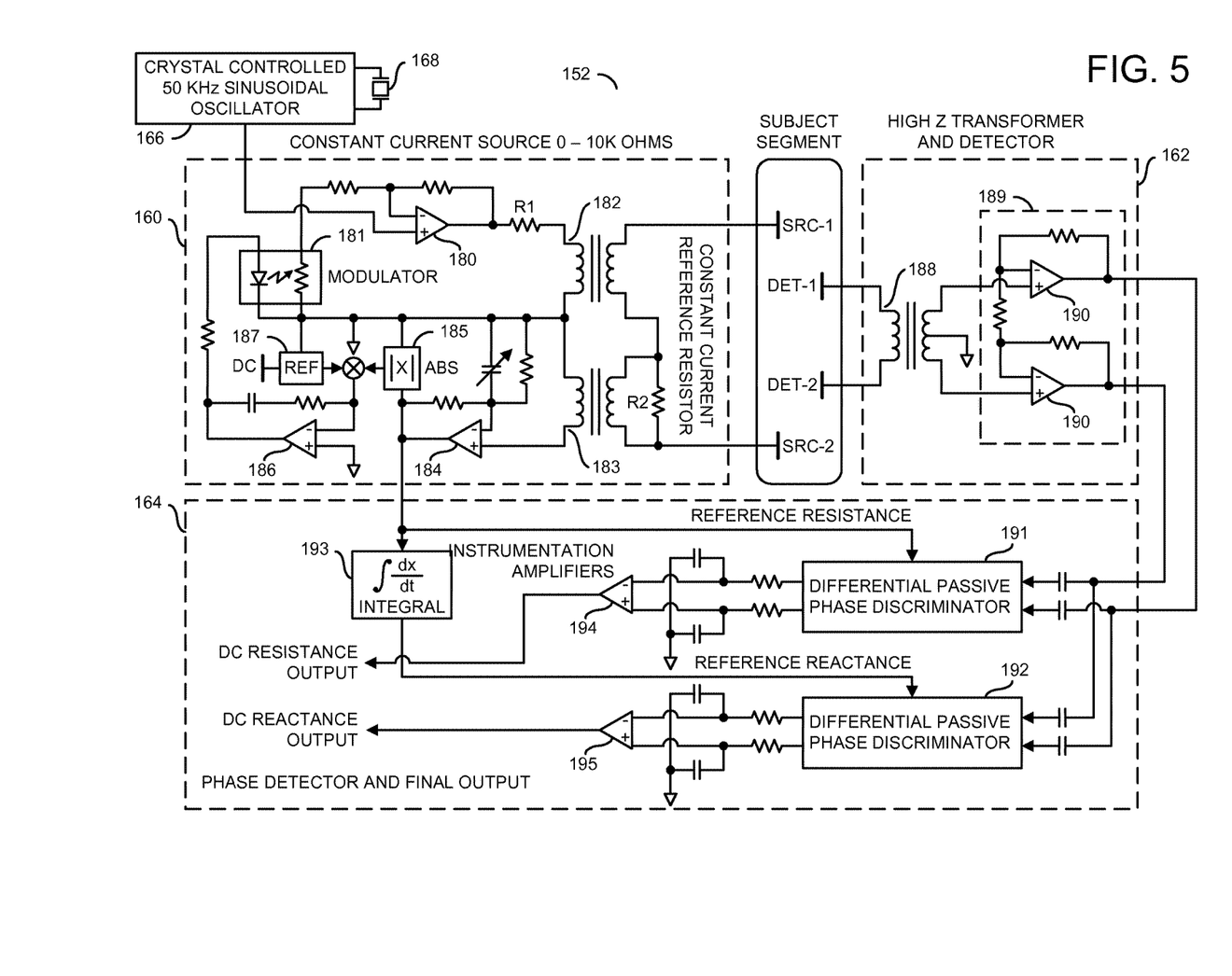
FIG. 5 is a diagram illustrating an example implementation of a BIA portion of the analysis circuit of FIG. 4.

Referring to FIG. 5, a diagram is shown illustrating an example implementation of the circuit 152 of FIG. 4. In various embodiments, the circuit 160 may receive a 50 KHz sinusoidal signal generated by a crystal controlled oscillator 166. The frequency of the sinusoidal signal from the crystal controlled oscillator 166 is determined by a crystal 168. However, other oscillator circuits may be implemented to meet the design criteria of a particular implementation. The circuit 160 is configured to maintain a current injected into the subject constant at a predetermined value (e.g., 425 microamps at 50 kHz). The maximum current should not exceed 500 microamps RMS at 50 kHz. To maintain a constant current, the circuit 160 supplies an input current to the subject (e.g., via the signals SRC-1 and SRC-2 of the interface 150), compares the current through the subject to a reference, and adjusts the input current based on the comparison. In one example, the circuit 160 implements a transformer coupled, open loop DC servo system that includes the oscillator 166, an amplifier 180, a modulator 181, a constant current input coupling transformer 182, a reference coupling transformer 183, a buffer amplifier 184, a rectifier 185, a summing amplifier 186, and a DC reference source 187.

The amplifier 180 is preferably configured as a non-inverting operational amplifier ("op-amp"). The sinusoidal output of the oscillator 166 is input into a non-inverting input of the amplifier 180 and an output of the amplifier 180 is coupled (fed back) to an inverting input through a resistor. A gain of the amplifier 180, and thus the current through the subject, is controlled by the modulator 181. The oscillator 166 can incorporate a conventional attenuator for the sinusoidal signal prior to the sinusoidal signal being presented to the amplifier 180.

The output of the amplifier 180 drives the constant current input coupling transformer 182, preferably through a series limiting resistor R1. The constant current input coupling transformer 182 supplies a current to the subject through electrodes connected to the interface 150. In one example, the constant current input coupling transformer 182 is implemented as a one-to-two transformer, where the primary is grounded, but the secondary is not.

A measuring circuit includes a constant current reference resistor R2, preferably a precision 1.0 kilo-ohm resistor, placed in the subject constant current path and coupled back to the remainder of the circuit 160 by the reference coupling transformer 183. In one example, the reference coupling transformer 183 is implemented as a one-to-one transformer, where the primary is ungrounded, but the secondary is grounded. Both the input coupling transformer 182 and the reference coupling transformer 183 should have an appropriate isolation barrier, such as a 500 volt DC isolation barrier. This configuration, together with the configuration of a detection transformer in the circuit 162, isolates the subject from all active circuitry.

The secondary of the reference coupling transformer 183 is coupled to a non-inverting input of the buffer amplifier 184. The buffer amplifier 184 is implemented, in one example, with a gain of preferably 6.5. An inverting input of the buffer amplifier 184 is grounded through a resistor in parallel with an adjustable capacitor. An output of the buffer amplifier 184 provides reference vectors for the circuit 164.

The output of the buffer amplifier 184, which is an indicator of the actual current flowing through the subject, is also used to derive a DC error signal used to control the modulator 181, which in turn controls the current through the subject to a predetermined value by controlling the gain of the amplifier 180. In various embodiments, the modulator 181 is an optocoupler including a light emitting diode (LED) optically coupled to a photocell. In one example, the photocell is a sealed cadmium sulfide (CdS) resistive conductor that changes resistance in response to light intensity from the LED. The DC error signal is supplied to an anode of the LED, while a cathode of the LED is grounded. The photocell resistance is high when the LED current is "off" and low when the LED current is "on." The resistive conductor is grounded on one end and connected to the inverting input of the amplifier 180 through another resistor. Although the modulator 181 could take the form of an FET, or some other device, an optocoupler is preferred because its use results in very little phase shift.

An output of the buffer amplifier 184 is rectified through a rectifier 185, producing a rectified voltage representing the actual current. The rectified voltage is compared in the summing amplifier 186 to a DC reference representing the desired current level. The DC reference is generated by a DC reference source 187. The summing amplifier 186 produces the DC error signal that drives the modulator 181. The DC error signal is a voltage that represents the difference between the actual current in the subject and the desired current. The DC reference source 187 should produce a very steady, fixed DC reference, preferably accomplished using a precision shunt regulator diode. In an alternative design, a standard Zener diode could be incorporated in place of the shunt regulator diode.

The summing amplifier 186 is a standard op-amp that compares the rectified signal from the rectifier 185 to the DC reference from the DC reference source 187. In one example, the summing amplifier 186 has a grounded non-inverting input. In one example, the precision rectified signal and the precision DC reference are supplied through resistors of the same value (e.g., 100 kilo-ohms) to the inverting input through a summing point, which point also includes the feedback supplied through a capacitor in series with a resistor to stabilize the constant current loop.

The detection of a voltage drop across the subject, and thus the first step in the measurement of the impedance, is performed by the circuit 162. In some embodiments, the circuit 162 includes a detection transformer 188 and an RF amplifier 189. The voltage drop across the subject is detected through electrodes connected to the DET-1 and DET-2 inputs of the interface 150. The unbalanced input from the subject is received at a primary of the detection transformer 188 and a balanced output is provided at a secondary of the detection transformer 188. In one example, the detection transformer 188 is a custom-wound transformer with an input impedance of greater than 2 megaohms at an operating frequency of 50 kHz. The detection transformer 188 provides no reference to ground in the subject, and the secondary is coupled to ground through a balanced center-tap.

The voltage from the secondary of the detection transformer 188 is amplified through the RF amplifier 89. In one example, the RF amplifier 189 comprises two op amps 190 configured as non-inverting common mode low-capacitance instrumentation amplifiers. Specifically, each tap from the secondary of the detection transformer 188 is connected to a non-inverting input of one of the op amps 190. The inverting inputs of the op amps 190 receive feedback through resistors, and the inverting inputs are coupled through another resistor, which controls the common mode gain. The subject variable differential outputs of the RF amplifier 189 are capacitively coupled to the circuit 164 through four coupling capacitors.

In some embodiments, the circuit 164 includes a phase detector 191 and a phase detector 192. Each of the phase detectors 191 and 192 is an identically designed balanced synchronous demodulator, except for the analog reference signal supplied to each. In one example, the phase detectors 191 and 192 are two passive analogue phase detectors that resolve the subject reactance and resistance obtained from the RF amplifier 189 through comparison to an analog reference reactance signal and an analog reference resistance signal. The output of each op amp 190 of the RF amplifier 189 provides one input to each of the phase detectors 191 and 192. Although the phase detectors shown are passive analogue detectors, an alternative embodiment can incorporate digital demodulators. However, the solid state demodulator is preferred for low power consumption and overall temperature stability.

As discussed previously, the output of the buffer amplifier 184 provides reference vectors for the circuit 164. Specifically, the buffer amplifier 84 provides a reference resistance vector and supplies an input into an integrator 193. The integrator 193 can be any standard device providing a 90 degree phase-shifted vector using the output of the buffer amplifier 184. An output of the integrator 193 provides a reference reactance vector. The reference resistance vector and the reference reactance vector supplied by the buffer amplifier 184 and the integrator 193, respectively, are each supplied to the phase detectors 191 and 192, respectively.

In general, the phase detectors 191 and 192 each include circuitry for demodulation and low pass filtering. The signals produced after demodulation and low pass filtering through the phase detectors 191 and 192 are two DC differential signals referenced to ground representing the resistance amplitude and two DC differential signals referenced to ground representing the reactance amplitude. These signals representing the resistance amplitude and the reactance amplitude are then converted to single-ended DC outputs by a pair of high quality instrumentation amplifiers 194 and 195. The resistance differential signals are input into the inverting and non-inverting inputs, respectively, of the amplifier 194, and the output of the amplifier 194 presents a DC Resistance Output signal. The reactance differential signals are input into the inverting and non-inverting inputs, respectively, of the amplifier 195, and an output of amplifier 195 presents a DC Reactance Output signal.

The resulting DC Resistance Output signal and DC Reactance Output signal from the instrumentation amplifiers 194 and 195 are supplied to the circuit 154, shown in FIG. 4. The DC Reactance Output signal and The DC Resistance Output signal could be, for example, voltage signals between zero and four volts, where four volts equals 2000 ohms.

Figure 6:
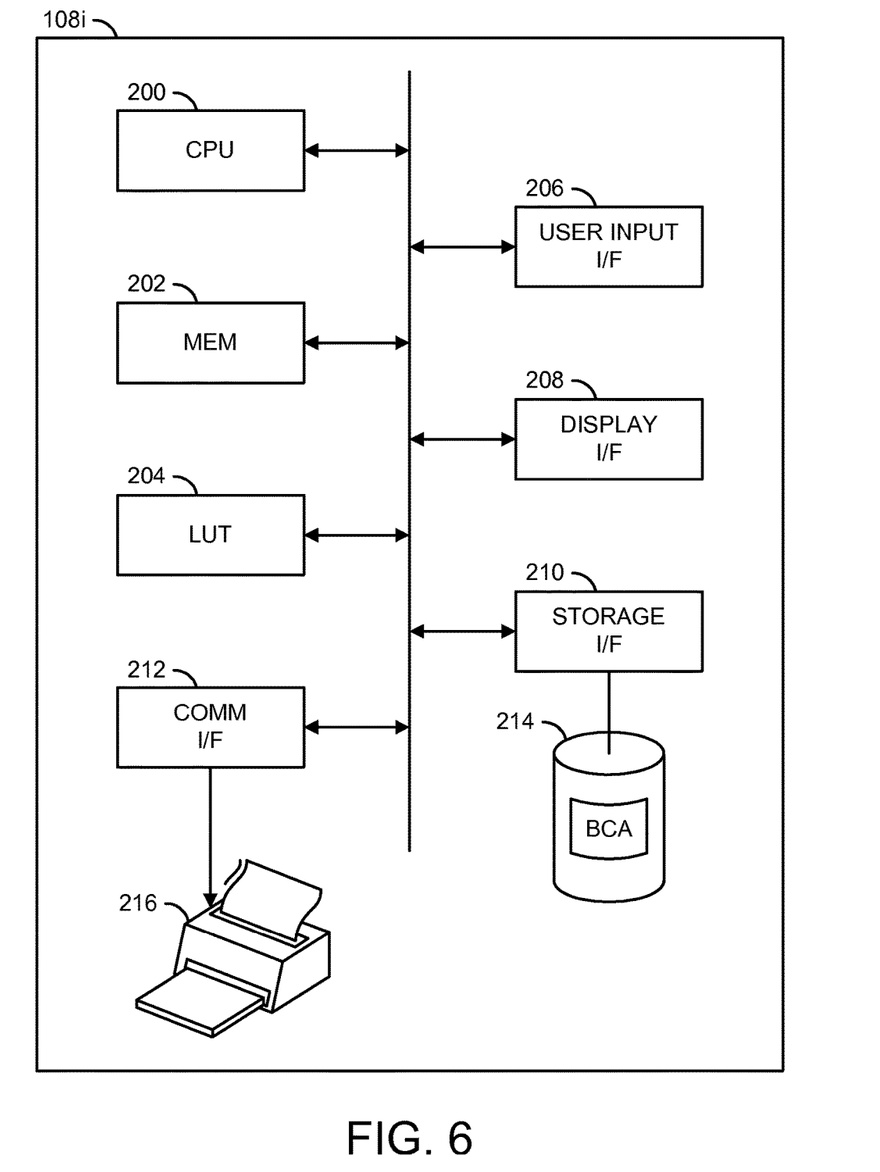
FIG. 6 is a diagram illustrating an example implementation of an electronic device of FIG. 1.

Referring to FIG. 6, a diagram is shown illustrating an example embodiment of an electronic device 108i. In various embodiments, the electronic device 108i may comprise a block (or circuit) 200, a block (or circuit) 202, a block (or circuit) 204, a block (or circuit) 206, a block (or circuit) 208, a block (or circuit) 210, and a block (or circuit) 212. The block 200 may implement a processor or central processing unit (CPU). The block 202 may be implemented as one or more types of memory (e.g., RAM, ROM, FLASH, etc.). The block 204 may implement a lookup table (LUT) containing predetermined coefficients for use with prediction equations in accordance with an embodiment of the invention. In some embodiments, the lookup table may be implemented using a removable media (e.g., thumb drive, flash memory card, etc.) to allow easy update of the coefficients. In some embodiments, the electronic devices are configured to update (e.g., flash) an internal memory to update the predetermined coefficients. The block 206 may implement a user input interface (I/F) circuit. The block 208 may implement a display or display I/F circuit. The circuit 210 may implement a storage interface (I/F) circuit. The circuit 212 may implement a communications interface (I/F) circuit. In one example, the block 210 may couple the electronic device 108i to one or more types of storage media (e.g., hard disk drive, flash drive, cloud storage, etc.) 214. In one example, the block 212 may couple the electronic device 108i to a printer 216.

The electronic device 108i may be controlled by an operating system (e.g., Microsoft Windows, Apple OS, Ubuntu, Linux, etc.) loaded from the storage media 214 and executed by the circuit 200. In various embodiments, the electronic devices 108a-108n store the number of predetermined coefficients used with the number of predictive equations in computing segmental body composition values in the lookup table 204. Each of the number of predictive equations expresses a correlation between a respective segmental body composition value and one or more of the plurality of segmental bioelectrical resistance and reactance measurements, such that segmental body composition values when added sum to a value essentially equal to respective whole body composition values. The computation of segmental body composition values using the number of predictive equations, the number of predetermined coefficients, the subject information, and the resistance and reactance values may be implemented in a body composition calculation application stored on the storage media 214. The block 212 may be configured to receive the subject information and the resistance and reactance values from the analysis circuit 106 and to produce body composition analysis reports in accordance with an embodiment of the invention using the printer 216.

Figure 7:
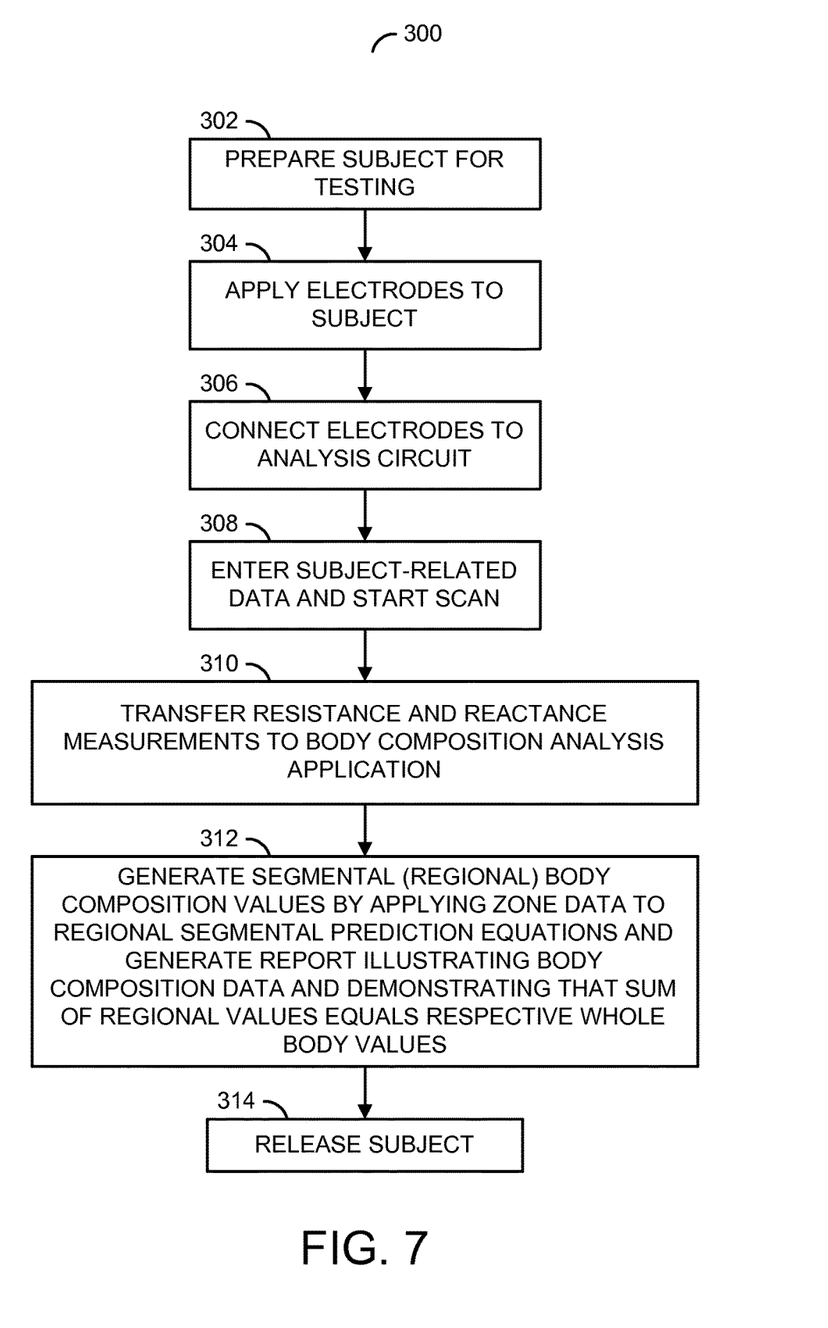
FIG. 7 is a flow diagram illustrating a process in accordance with an embodiment of the invention.

Referring to FIG. 7, a flow diagram is shown illustrating a process in accordance with an example embodiment of the present invention. In some embodiments, a process (or method) 300 in accordance with an example embodiment of the present invention may be implemented. The process 300 may comprise a step (or state) 302, a step (or state) 304, a step (or state) 306, a step (or state) 308, a step (or state) 310, a step (or state) 312, and a step (or state) 314. In the step 302, a subject is prepared for testing by having the subject remove shoes and socks and lay in a supine position on a non-conductive surface (e.g., an examination table). In the step 304, eight electrodes are applied to the subject as described above in connection with FIG. 1. In the step 306, each of the electrodes is connected to an analysis circuit. In one example, leads from a multiplexer circuit are attached to each of the electrodes and the multiplexer circuit is then connected to an analysis circuit. In another example, the electrodes are connected to leads directly from the analysis circuit. In some embodiments, the leads may be grouped (e.g., right side and left side) for the convenience of the operator. In the step 308, subject-related information (e.g., age, name, height, weight, gender, etc.) are entered into the analysis circuit and a scan is started to collect resistance and reactance measurements (e.g., 13 zones, 26 measurements). In the step 310, the resistance and reactance measurements are transferred to an electronic device (e.g., a PC, etc.) or time and date stamped and stored in the analysis circuit for later transfer to the electronic device (e.g., en masse) via a communication link (e.g., a USB connection, a WiFi connection, a BlueTooth (BT) connection, a flash card, a thumb drive, etc.). In the step 312, the electronic device is configured, by an application program, to generate segmental (regional) body composition values by applying the zone data to regional segmental prediction equations and generate a report illustrating numerical and graphical representations of the segmental (regional) body composition values, as well as demonstrate that sums of regional total mass, lean mass, fat mass, and fat percent are essentially equal to respective whole body values. In the step 314, the subject is allowed to sit up and put their shoes and socks back on.

Figure 8:
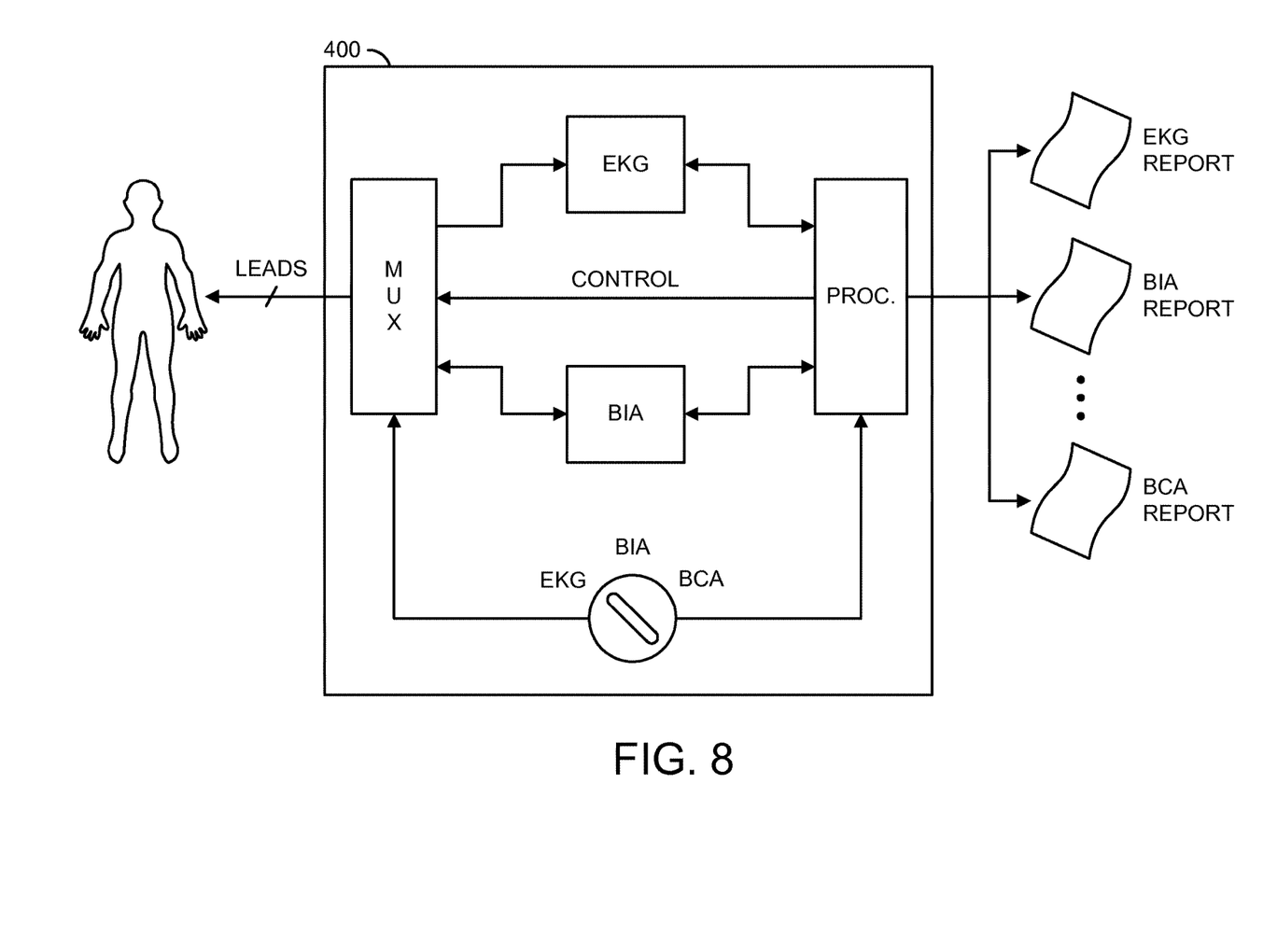
FIG. 8 is a diagram illustrating a system in accordance with another example embodiment of the invention.

Referring to FIG. 8, a diagram of a system 400 is shown illustrating an integrated bioelectrical analysis system in accordance with another example embodiment of the invention. In one example, the system 400 may be configured to perform one or more of an electrocardiogram (EKG or ECG), a bioelectrical impedance analysis (BIA), and/or a body composition analysis (BCA), and automatically generate the appropriate report(s). For example, the same electrodes may be used to produce 4-lead EKG, BIA, and BCA reports.

The functions illustrated by the diagrams of FIGS. 1-8 may be implemented using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), video digital signal processor (VDSP) and/or similar computational machines, programmed according to the teachings of the specification, as will be apparent to those skilled in the relevant art(s). Appropriate software, firmware, coding, routines, instructions, opcodes, microcode, and/or program modules may readily be prepared by skilled programmers based on the teachings of the disclosure, as will also be apparent to those skilled in the relevant art(s). The software is generally executed from a medium or several media by one or more of the processors of the machine implementation.

The invention may also be implemented by the preparation of ASICs (application specific integrated circuits), Platform ASICs, FPGAs (field programmable gate arrays), PLDs (programmable logic devices), CPLDs (complex programmable logic devices), sea-of-gates, RFICs (radio frequency integrated circuits), ASSPs (application specific standard products), one or more monolithic integrated circuits, one or more chips or die arranged as flip-chip modules and/or multi-chip modules or by interconnecting an appropriate network of conventional component circuits, as is described herein, modifications of which will be readily apparent to those skilled in the art(s).

The invention thus may also include a computer product which may be a storage medium or media and/or a transmission medium or media including instructions which may be used to program a machine to perform one or more processes or methods in accordance with the invention. Execution of instructions contained in the computer product by the machine, along with operations of surrounding circuitry, may transform input data into one or more files on the storage medium and/or one or more output signals representative of a physical object or substance, such as an audio and/or visual depiction. The storage medium may include, but is not limited to, any type of disk including floppy disk, hard drive, magnetic disk, optical disk, CD-ROM, DVD and magneto-optical disks and circuits such as ROMs (read-only memories), RAMs (random access memories), EPROMs (erasable programmable ROMs), EEPROMs (electrically erasable programmable ROMs), UVPROM (ultra-violet erasable programmable ROMs), Flash memory, magnetic cards, optical cards, and/or any type of media suitable for storing electronic instructions.

The elements of the invention may form part or all of one or more devices, units, components, systems, machines and/or apparatuses. The devices may include, but are not limited to, servers, workstations, storage array controllers, storage systems, personal computers, laptop computers, notebook computers, palm computers, personal digital assistants, portable electronic devices, battery powered devices, set-top boxes, encoders, decoders, transcoders, compressors, decompressors, pre-processors, post-processors, transmitters, receivers, transceivers, cipher circuits, cellular telephones, digital cameras, positioning and/or navigation systems, medical equipment, heads-up displays, wireless devices, audio recording, audio storage and/or audio playback devices, video recording, video storage and/or video playback devices, game platforms, peripherals and/or multi-chip modules. Those skilled in the relevant art(s) would understand that the elements of the invention may be implemented in other types of devices to meet the criteria of a particular application.

The terms "may" and "generally" when used herein in conjunction with "is(are)" and verbs are meant to communicate the intention that the description is exemplary and believed to be broad enough to encompass both the specific examples presented in the disclosure as well as alternative examples that could be derived based on the disclosure. The terms "may" and "generally" as used herein should not be construed to necessarily imply the desirability or possibility of omitting a corresponding element.

While the invention has been particularly shown and described with reference to the preferred embodiments thereof, it will be understood by those skilled in the art that various changes in form and details may be made without departing from the scope of the invention.

The invention claimed is:

1. An apparatus comprising:
an analysis circuit configured to automatically make a plurality of segmental bioelectrical resistance and reactance measurements using permutations of eight electrodes selected four at a time, wherein (i) the analysis circuit is further configured to utilize a constant current source to maintain an input current, which is injected into a subject, constant at a predetermined value by supplying the input current to the subject via a first pair of the four selected electrodes, comparing the current through said subject to a reference, and adjusting the input current based on the comparison, and (ii) said eight electrodes are configured to be attached to predetermined locations on a body of said subject while in a supine position; and a controller configured to (i) calculate a plurality of segmental body composition values and a plurality of whole body composition values using said plurality of segmental bioelectrical resistance measurements, a number of predetermined coefficients, a height of said subject, a weight of said subject, a gender of said subject, and a number of predictive equations, and (ii) generate a report presenting at least one set of said plurality of segmental body composition values and said whole body composition values, wherein (i) said number of predetermined coefficients are stored in a lookup table, (ii) each of said number of predictive equations expresses a correlation between a respective segmental or respective whole body composition value and one or more of said plurality of segmental bioelectrical resistance measurements, such that a sum of a set of individual segmental body composition values is essentially equal to a respective whole body composition value, allowing each value in the set to be calculated from the other values in the set and the respective whole body composition value, (iii) said plurality of segmental body composition values comprises sets of lean mass values, no bone mass values, and fat mass values, and (iv) said lean mass values are calculated using an equation having a general form of Segmental Lean Mass Value=$C1*\exp(C2*\log(\text{segmental bioelectrical resistance measurement})+C3*\log(\text{height})-C4)+C5*\text{weight}-C6$, where the coefficients $C1$ through $C6$ represent predetermined coefficients, corresponding to respective body segments, stored in said lookup table.

2. The apparatus according to claim 1, wherein said number of predetermined coefficients stored in said lookup table are generated based upon data collected using a gold standard method for determining body composition.

3. The apparatus according to claim 2, wherein said gold standard method for determining body composition comprises dual-energy x-ray absorptiometry (DEXA).

4. The apparatus according to claim 1, further comprising an interface circuit configured to connect said analysis circuit to said electrodes.

5. The apparatus according to claim 4, wherein said interface circuit comprises an isolated low capacitance multiplexer circuit configured to select said permutations of said eight electrodes selected four at a time in response to a control signal from said analysis circuit.

6. The apparatus according to claim 1, wherein said electrodes comprise stick on electrodes.

7. The apparatus according to claim 1, wherein said analysis circuit comprises:
a first circuit configured to induce said input current along a first path through said body of said subject from a first electrode connected to a first point on said body of said subject to a second electrode connected to a second point on said body of said subject; and
a second circuit configured to measure an electrical characteristic along a second path from a third electrode connected to a third point on said body of said subject to a fourth electrode connected to a fourth point on said body of said subject, wherein said electrical characteristic represents a value corresponding to a virtual intersection of said first path and said second path.

8. The apparatus according to claim 1, further comprising a multiplexer circuit configured to select said four electrodes, wherein a first electrode, a second electrode, a third electrode, and a fourth electrode are selected from a first group of three of said eight electrodes, a second group of three of said eight electrodes, a third group of three of said eight electrodes, and a fourth group of three of said eight electrodes, respectively.

9. The apparatus according to claim 1, wherein pairs of electrodes of said eight electrodes are attached to each extremity of said body of said subject with a current source electrode of each pair being more distal than a detecting electrode of each pair.

10. The apparatus according to claim 7, wherein said first electrode connected to said first point and said third electrode connected to said third point are placed on opposite sides of an anatomical joint of said body of said subject.

11. The apparatus according to claim 1, wherein said eight electrodes are placed on one or more of a finger, a wrist, a forearm, an upper arm, a toe, an ankle, a lower leg, and an upper leg.

12. The apparatus according to claim 1, wherein said electrodes are placed on a dorsal portion of the skin of said body of said subject.

13. The apparatus according to claim 1, wherein said predictive equations comprise a set of equations for each arm that includes:
  an equation determining right arm lean mass (RALM) and left arm lean mass (LALM) values of the form xALM=C1*exp(C2*log(right or left arm resistance)+C3*log(Height)−C4)+C5*Weight−C6;
  an equation determining right arm mass (RAM) and left arm mass (LAM) values of the form xAM=exp(C7*log(Weight)+C8*log(xALM)−C9);
  an equation determining right arm no bone mass (RANBM) and left arm no bone mass (LANBM) values of the form xANBM=exp(C10*log(Weight)+C11*log(xALM)−C12); and
  an equation determining right arm fat mass (RAFM) and left arm fat mass (LAFM) values of the form xAFM=xANBM−xALM, where the coefficients C1 through C12 represent predetermined coefficients corresponding to a respective arm stored in said lookup table.

14. The apparatus according to claim 1, wherein said predictive equations comprise a set of equations for each leg that includes:
  an equation determining right leg lean mass (RLLM) and left leg lean mass (LLLM) values of the form xLLM=C1*exp(C2*log(right or left leg resistance)+C3*log(Height)−C4)+C5*Weight−C6;
  an equation determining right leg mass (RLM) and left leg mass (LLM) values of the form xLM=exp(C7*log(Weight)+C8*log(xLLM)−C9);
  an equation determining right leg no bone mass (RLNBM) and left leg no bone mass (LLNBM) values of the form xLNBM=C10*(Weight)+C11; and
  an equation determining right leg fat mass (RLFM) and left leg fat mass (LLFM) values of the form xLFM=C12*(xLNBM−xLLM)−C13*(Gender)+C14, where the coefficients C1 through C14 represent predetermined coefficients corresponding to a respective leg stored in said lookup table.

15. The apparatus according to claim 1, wherein said predictive equations comprise a set of equations for each side of the body that includes:
  an equation determining right side lean mass (RSLM) and left side lean mass (LSLM) values of the form xSLM=C1*exp (C2*log(right or left body resistance)+C3*log(Height)−C4)+C5*Weight−C6;
  an equation determining right side mass (RSM) and left side mass (LSM) values of the form xSM=exp(C7*log(Weight)+C8*log(xSLM)−C9);
  an equation determining right side no bone mass (RSNBM) and left side no bone mass (LSNBM) values of the form xSNBM=C10*(Weight)+C11; and
  an equation determining right side fat mass (RSFM) and left side fat mass (LSFM) values of the form xSFM=xSNBM−xSLM, where the coefficients C1 through C11 represent predetermined coefficients corresponding to a respective side of the body stored in said lookup table.

16. The apparatus according to claim 1, wherein said predictive equations comprise a set of equations for upper and lower segments of the body that includes:
  an equation determining upper body lean mass (UBLM) and lower body lean mass (LBLM) values of the form xBLM=C1*exp(C2*log(upper or lower body resistance)+C3*log(Height)−C4)+C5*Weight−C6;
  an equation determining upper body mass (UBM) and lower body mass (LBM) values of the form xBM=C7*(Weight)−C8*(Gender)+C9;
  an equation determining upper body no bone mass (UBNBM) and lower body no bone mass (LBNBM) values of the form xBNBM=C10*(Weight)−C11*(Gender)+C12; and
  an equation determining upper body fat mass (UBFM) and lower body fat mass (LBFM) values of the form xBFM=xBNBM−xBLM, where the coefficients C1 through C12 represent predetermined coefficients corresponding to a respective body segments stored in said lookup table.

17. The apparatus according to claim 1, wherein said predictive equations comprise a set of equations for right torso and left torso segments of the body that includes:
  an equation determining right torso lean mass (RTLM) and left torso lean mass (LTLM) values of the form xTLM=xSLM−(xALM+xLLM);
  an equation determining right torso mass (RTM) and left torso mass (RTM) values of the form xTM=xSM−(xAM+xLM);
  an equation determining right torso no bone mass (RTNBM) and left torso no bone mass (RTNBM) values of the form xTNBM=xSNBM−(xANBM+xLNBM); and
  an equation determining right torso fat mass (RTFM) and left torso fat mass (LTFM) values of the form xTFM=xTNBM−(xSLM−xALM−xLLM).

18. The apparatus according to claim 1, wherein said predictive equations comprise a set of equations for whole body values that includes:
  an equation determining a whole body lean mass (WBLM) value of the form WBLM=C1*exp(C2*log(avg(right body resistance+left body resistance))+C3*log(Height)−C4)+C5*Weight−C6;
  an equation determining a whole body mass (WBM) value of the form WBM=C7*(Weight)−C8*(Gender)+C9;
  an equation determining a whole body no bone mass (WBNBM) value of the form WBNBM=C10*(Weight)−C11*(Gender)+C12; and
  an equation determining a whole body fat mass (WBFM) value of the form WBFM=WBNBM−WBLM, where the coefficients C1 through C12 represent predetermined whole body coefficients stored in said lookup table (LUT).

19. A method of determining a body composition parameter of a human body comprising the steps of:

connecting first and second electrodes to a first point and a second point, respectively, on a first extremity of said human body;
connecting third and fourth electrodes to a third point and a fourth point, respectively, on a second extremity of said human body;
connecting fifth and sixth electrodes to a fifth point and a sixth point, respectively, on a third extremity of said human body;
connecting seventh and eighth electrodes to a seventh point and a eighth point, respectively, on a fourth extremity of said human body;
automatically making a plurality of segmental bioelectrical resistance and reactance measurements using permutations of the first, second, third, fourth, fifth, sixth, seventh, and eighth electrodes selected four at a time, wherein said plurality of segmental bioelectrical resistance and reactance measurements involve using a constant current source to maintain an input current, which is injected into said human body, constant at a predetermined value by supplying the input current to said human body via a first pair of the four selected electrodes, comparing the current through said human body to a reference, and adjusting the input current based on the comparison; and
using an electronic device to (i) calculate a plurality of segmental body composition values and a plurality of whole body composition values using said plurality of segmental bioelectrical resistance measurements, a number of predetermined coefficients, a height of said human body, a weight of said human body, a gender of said human body, and a number of predictive equations, and (ii) generate a report presenting at least one set of said plurality of segmental body composition values and said whole body composition values,
wherein (i) said number of predetermined coefficients are stored in a lookup table of said electronic device, (ii) each of said number of predictive equations expresses a correlation between a respective segmental or respective whole body composition value and one or more of said plurality of segmental bioelectrical resistance measurements, such that a sum of a set of individual segmental body composition values is essentially equal to a respective whole body composition value, allowing each value in the set to be calculated from the other values in the set and the respective whole body composition value, (iii) said plurality of segmental body composition values comprises sets of lean mass values, no bone mass values, and fat mass values, and (iv) said lean mass values are calculated using an equation having a general form of Segmental Lean Mass Value=$C1*\exp(C2*\log(\text{segmental bioelectrical resistance measurement})+C3*\log(\text{height})-C4)+C5*\text{weight}-C6$, where the coefficients C1 through C6 represent predetermined coefficients, corresponding to respective body segments, stored in said lookup table.

20. The method according to claim 19, wherein current source electrodes are placed more distal from a core of said human body than detecting electrodes.

* * * * *